(12) United States Patent
Gesler, III

(10) Patent No.: US 7,981,087 B2
(45) Date of Patent: Jul. 19, 2011

(54) WINGED SECUREMENT DEVICE

(75) Inventor: William G. Gesler, III, New Hudson, MI (US)

(73) Assignee: Centurion Medical Products Corporation, Williamston, MI (US)

( * ) Notice: Subject to any disclaimer, the term of this patent is extended or adjusted under 35 U.S.C. 154(b) by 1438 days.

(21) Appl. No.: 11/230,433

(22) Filed: Sep. 20, 2005

(65) Prior Publication Data

US 2007/0078400 A1   Apr. 5, 2007

(51) Int. Cl.
*A61M 5/32* (2006.01)

(52) U.S. Cl. .. 604/174; 604/177; 604/180; 128/DIG. 26

(58) Field of Classification Search ................ 604/174, 604/177, 178, 180, 164.04, 179; 128/DIG. 6, 128/DIG. 26

See application file for complete search history.

(56) References Cited

U.S. PATENT DOCUMENTS

| | | | | |
|---|---|---|---|---|
| 3,834,380 A | * | 9/1974 | Boyd | 604/180 |
| 4,129,128 A | * | 12/1978 | McFarlane | 604/180 |
| 5,147,320 A | * | 9/1992 | Reynolds et al. | 604/174 |
| 5,755,225 A | * | 5/1998 | Hutson | 128/207.18 |
| 6,224,571 B1 | * | 5/2001 | Bierman | 604/174 |
| 6,290,676 B1 | * | 9/2001 | Bierman | 604/174 |
| 6,582,403 B1 | * | 6/2003 | Bierman et al. | 604/174 |
| 2004/0138624 A1 | * | 7/2004 | Bierman | 604/174 |
| 2008/0045905 A1 | * | 2/2008 | Chawki | 604/174 |

* cited by examiner

*Primary Examiner* — Theodore Stigell
*Assistant Examiner* — Shefali Patel
(74) *Attorney, Agent, or Firm* — Fildes & Outland, P.C.

(57) ABSTRACT

A winged securement device includes a flexible base having an adhesive side and an opposite non-adhesive side. A generally planar, integral elastomeric anchoring member is mounted on the base non-adhesive side. The anchoring member includes a pair of opposing gripping tabs formed therein the anchoring member and a slit disposed between the tabs. The gripping tabs may be pulled to open the slit for receiving wings of a catheter hub therein and for securing the wings between the anchoring member and the base.

16 Claims, 3 Drawing Sheets

WINGED SECUREMENT DEVICE

TECHNICAL FIELD

This invention relates to catheter securement devices, and more particularly to securement devices for securing catheters to a patient's skin.

BACKGROUND OF THE INVENTION

It is known in the art relating to catheters that after insertion of a catheter through a patient's skin into a vein, the catheter must be secured to prevent the catheter from slipping out of the patient's vein. Commonly, surgical tape is used to hold the catheter hub or tubing connected to the catheter to the patient's skin. Oftentimes, this method is ineffective to permanently, securely anchor the catheter and to prevent catheter movement.

Further, inadvertent movement of a catheter while the catheter is inserted in a vein is a leading cause of premature catheter failure. When a catheter moves in a vein, it scrapes and pokes the inner wall of the vein, thereby irritating the vein. Repeated movement of the catheter thereby causes sufficient irritation of the vein to require the catheter to be removed and a new catheter inserted in a different location along the same vein or in an entirely new vein. This is costly as it results in a waste of resources. Also, repeated movement of an inserted catheter can cause migration of the catheter in the vein or worse, may lead to the catheter being removed from the vein. Therefore, a need exists for effective anchoring/securement devices for catheters.

Moreover, catheter insertion sites are often dressed with a dressing to protect the insertion site from infection and the like. As a matter of course, these dressings as well as the catheter anchoring means (e.g., tape) must be periodically removed and replaced. For example, dressings and anchoring means may be routinely changed on a weekly basis. The catheter itself, however, if not disturbed, in certain cases can be reanchored, redressed, and left in the vein for a longer period of time. Removal of expired anchoring means and dressings, however, can undesirably cause disturbance/movement of the catheter to the point that the catheter must be removed and replaced. Therefore, a need exists for an anchoring means that can be removed from the catheter without damaging the catheter.

SUMMARY OF THE INVENTION

The present invention provides a catheter securement device that securely anchors a catheter to a patient's skin while at the same time is easily removed from the catheter without damaging the catheter or disturbing the catheter insertion site. The present catheter securement device is designed to be, used to anchor catheters having wings, such as suture wings extending from a hub of the catheter. For example, one intended use of the present catheter securement device is to secure PICCs (Peripherally Inserted Central Catheters), but the catheter securement device may be used to secure any winged-type catheter. The present catheter securement device prevents stresses applied to the catheter hub or luer connectors attached to the catheter from transferring to the catheter insertion site and causing catheter migration or removal as well as insertion site irritation.

More particularly, a winged securement device in accordance with the present invention includes a flexible base having an adhesive side and an opposite non-adhesive side. A planar, integral elastomeric anchoring member is mounted on the base non-adhesive side. The anchoring member includes a pair of opposing gripping tabs formed therein the member and a slit disposed between the tabs. The gripping tabs may be pulled, deforming the anchoring member, to open the slit for receiving wings of a catheter hub therein and for securing the wings between the anchoring member and the base.

In a specific embodiment, cut lines may define the gripping tabs and the cut lines may be C-shaped. The anchoring member may include apertures at terminal ends of the cut lines. The anchoring member may also include apertures at terminal ends of the slit. The anchoring member may be adhered to the base along a peripheral edge of the anchoring member. The anchoring member may be made of one of silicone and polyurethane, or any other similar material. The base may be a foam pad or similar material. The securement device may include a recess in an edge thereof along a line extending through the slit. The securement device may be generally oval in shape with the slit generally extending along the minor axis thereof.

The securement device may also include a release liner having a tackless side contacting the adhesive side of the base, the release liner generally extending to an edge of the base. Optionally, the release liner may include a first piece and a second piece, the first and second pieces being folded such that each of the first and second pieces have a tab formed by the fold. One of the pieces can be released from the dressing without tampering with the other of the pieces.

In an alternative embodiment, a winged securement device in accordance with the present invention includes a flexible sheet-like base having an adhesive side and an opposite non-adhesive side. A planar, integral elastomeric anchoring layer member is mounted on the base non-adhesive side. The anchoring member includes at least one slit and a pair of opposing gripping tabs formed therein the member, each gripping tab being adjacent one of the at least one slit. The gripping tabs may be pulled to open the at least one slit for receiving wings of a catheter hub therein and for securing the wings between the anchoring member and the base.

Optionally, the anchoring member may include cut lines defining said tabs. The anchoring member may also include apertures at terminal ends of the cut lines as well as apertures at terminal ends of each of the at least one slit. The anchoring member may be adhered to the base along a peripheral edge of said anchoring member. The second embodiment of the securement device may also include any of the other optional features described in the first embodiment.

These and other features and advantages of the invention will be more fully understood from the following detailed description of the invention taken together with the accompanying drawings.

DETAILED DESCRIPTION OF THE INVENTION

Figure 1:
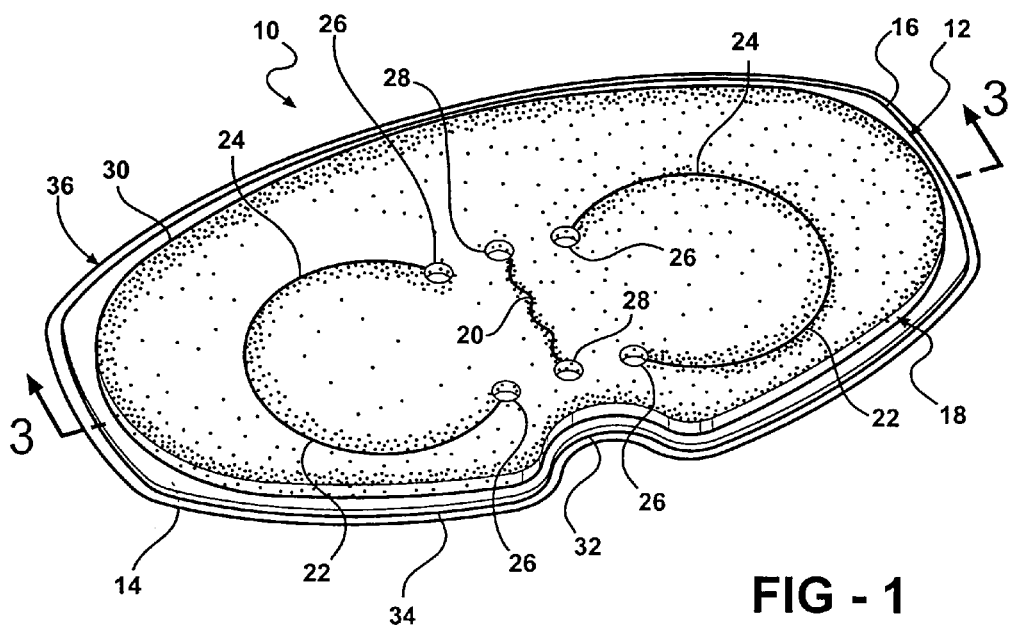
FIG. 1 is a perspective view of a winged securement device in accordance with the present invention.

Referring now to the drawings in detail, numeral 10 generally indicates a winged securement device in accordance with the present invention. A bottom side of the securement device 10 can be adhered to a patient's skin. The securement device 10 then anchors a catheter by urgedly engaging catheter hub wings of a catheter inserted into a patient. Once the catheter is secured by the securement device 10, stresses and forces applied on luers and fittings connected to the catheter will not cause the catheter to move and thereby irritate the insertion site. The catheter wings are also easily removable from the securement device 10, allowing for replacement of the securement device without disturbing the catheter inserted in the insertion site.

Figure 2:
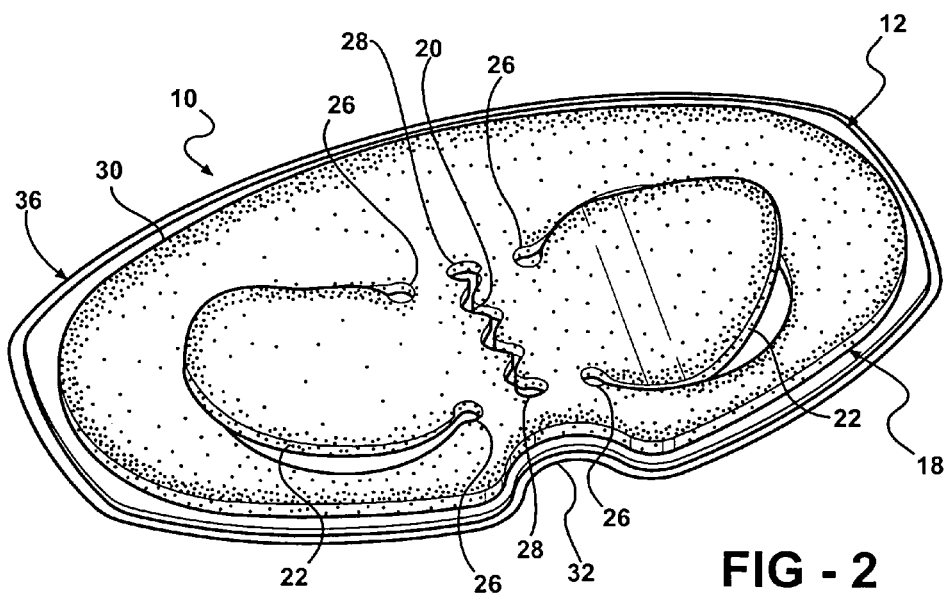
FIG. 2 is a perspective view of the winged securement device of FIG. 1 illustrating opening of an anchoring member slot by a pulling force on an anchoring member tab.
Figure 3:
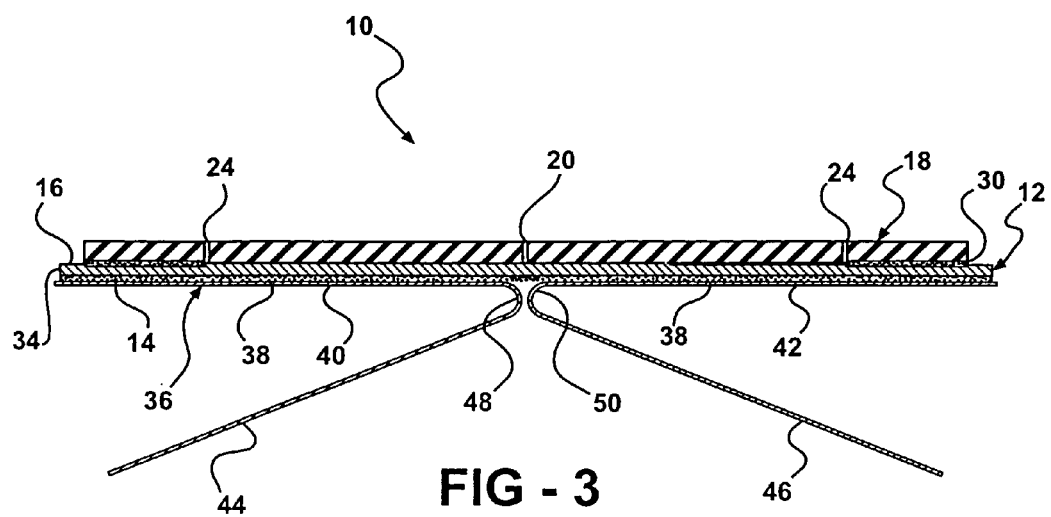
FIG. 3 is a cross-sectional view of the winged securement device taken along the line 3-3 in FIG. 1.

Turning first to FIGS. 1 through 3, a winged securement device 10 in accordance with the present invention includes a flexible base 12 having an adhesive side 14 and an opposite non-adhesive side 16. The adhesive on the base adhesive side 14 may be any suitable medical grade adhesive or similar. The base 12 may be sheet-like, such as a layer of material, and may be a foam pad or similar material such as microfoam or the like. A planar, integral elastomeric anchoring member 18 is mounted on the base non-adhesive side 16. The anchoring member 18 is formed from a single piece of material. The anchoring member 18 may be made of one of silicone and polyurethane, high friction rubber, or any other similar material that exhibits elasticity and/or resiliency. Similar to the base 12, the anchoring member 18 may also be formed as a layer of material, although in the embodiment shown in FIGS. 1 through 3, the anchoring member 18 has a greater thickness than the base 12. Generally, however, the anchoring member 18 and base 12 may have similar size and shape. Also, the anchoring member 18 and the base 12 may be integral with each other, and the base may then be made of the same material as the anchoring member.

Figure 4:
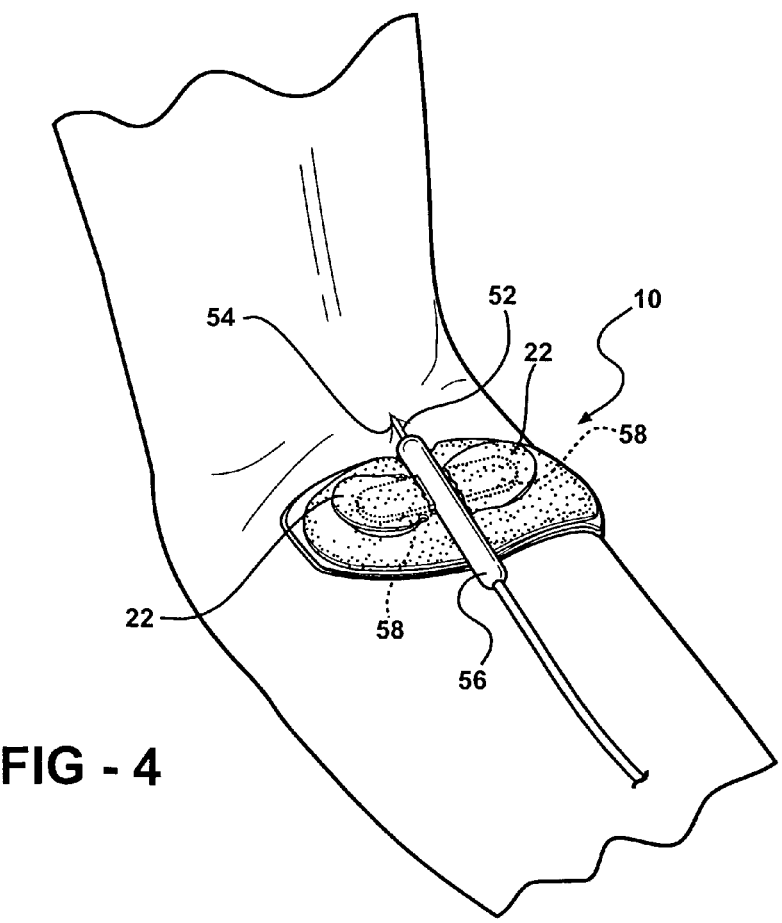
FIG. 4 is an environmental view of the winged securement device of FIG. 1 illustrating the securement device adhered to a patient's skin, and a catheter hub secured in the securement device.

The anchoring member 18 includes a pair of opposing gripping tabs 22 formed therein the member 18 and a slit 20 disposed between said gripping tabs 22. The gripping tabs 22 are generally adjacent the slit 20 and may also be referred to as wings. The anchoring member 18 may alternatively include more than one slit 20, and each gripping tab 22 may be adjacent one of the slits. For example, the anchoring member 18 could include two slits 20, and each of the pair of gripping tabs 22 could be adjacent one of the two slits. The slit 20 may be centrally disposed in the anchoring member 18, though the slit 20 may instead be offset from the center of the anchoring member 18. The gripping tabs 22 may be pulled to open the slit(s) 20 for receiving wings of a catheter hub therein and for securing the wings between the anchoring member 18 and the base 12 (as shown and described later with reference to FIG. 4).

In a specific embodiment, cut lines 24 may define the gripping tabs 22 and the cut lines 24 may be C-shaped or a similar shape such as a U-shape, spade shape, etc. The cut lines 24 may be formed by die-cutting the device 10. The securement device 10, however, may also be made by injection molding or casting, in which case the cut lines 24 would instead be separation lines formed in the molding or cast. The anchoring member 18 may further include apertures 26 at terminal ends of the cut lines 24. The anchoring member 18 may also include apertures 28 at terminal ends of the slit 20. Pulling forces exerted on the gripping tabs 22 stretch portions of the anchoring member 18 around the terminal ends of the cut lines 24 and the terminal ends of the slit 20, which potentially could cause tearing of the anchoring member 18. The apertures 26, 28 help to eliminate the tendency of the anchoring member 18 to tear when the gripping tabs 22 are pulled by opening such that the angular circumferences of the apertures flex towards a straight line.

The anchoring member 18 may be adhered to the base 12 along a peripheral edge 30 of the anchoring member 18. In this arrangement, there is no adhesive between the base 12 and the anchoring member 18 generally around an inner portion of the anchoring member 18 such that when the gripping tabs 22 are pulled, the anchoring member 18 may be pulled away from the base 12 to create a gap between the anchoring member and base.

The securement device 10 may include a recess 32 in an edge 34 thereof along a line in space extending through the slit 20. The securement device 10 may be generally oval in shape in two dimensions (i.e., length and width). The slit 20 may generally extend along the minor axis of the securement device 10. The securement device 10 may have other shapes, however, such as a square shape, a rectangular shape, an oblong shape, or similar.

The securement device 10 may also include a release liner 36 having a tackless side 38 contacting the adhesive side 14 of the base 12. The release liner 36 generally extends to an edge of the base 12. Optionally, the release liner 36 may include a first piece 40 and a second piece 42. The first and second pieces 40, 42 may be folded such that each of the first and second pieces have tabs 44, 46 formed by the folds 48, 50. One of the pieces 40, 42 can be released from the dressing without tampering with the other piece.

With reference now to FIGS. 1 through 4, for purposes of example the winged securement device 10 is shown securing a PICC 52 (Peripherally Inserted Central Catheter). First, a health care provider, herein a nurse for illustrative purposes, inserts the catheter 52 through a patient's skin into one of the patient's veins at an insertion site 54. After insertion of the catheter 52, the nurse removes one piece 40 of the release liner 36 by pulling on the release liner tab 44. This exposes part of the adhesive side 14 of the base 12, which the nurse mounts on the patient's skin such that the slit 20 is positioned below the catheter hub 56 and the gripping tabs 22 are generally positioned below the catheter hub wings 58. The nurse then removes the other piece 42 of the release liner 36 by pulling on the release liner tab 46 to expose the rest of the adhesive side 14 of the base 12. The base 12 is then fully adhered to the patient's skin.

At this point, the nurse may hold the catheter 52 in place with one finger and use his/her other hand to pull on one of the gripping tabs 22. Pulling on a gripping tab 22 opens the slit 20 as shown in FIG. 2. The catheter wing 58 above the pulled gripping tab 22 is inserted through the slit 20 so that it is disposed underneath the gripping tab 22. The nurse then releases the gripping tab 22, which secures the catheter wing 58. After securing one catheter wing 58, the nurse repeats the above steps to secure the other catheter wing. The gripping tabs 22 engage the catheter wings 58, and the elasticity of the gripping tabs 22 provides a constant force against the catheter wings to hold the catheter wings between the gripping tabs 22 of the anchoring member 18 and the non-adhesive side 16 of the base 12. Due to the material of construction of the anchoring member 18, there is also a significant amount of friction between the gripping tabs 22 and the catheter wings 58, which also aids in preventing movement of the catheter 52.

Figure 5:
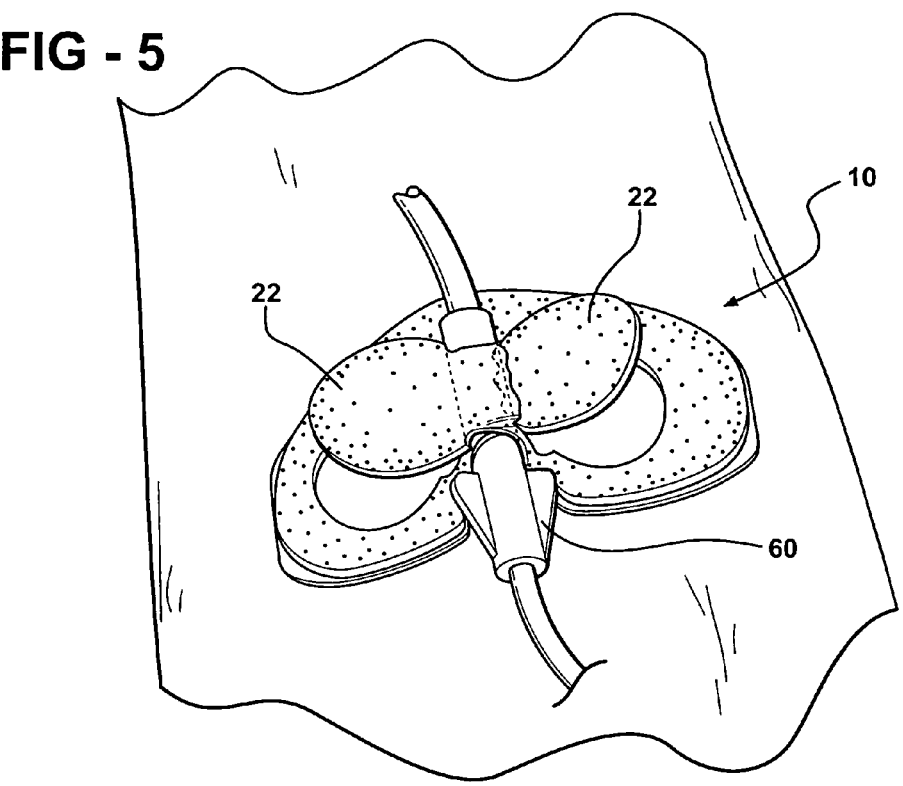
FIG. 5 is an environmental view of the winged securement device of FIG. 1 illustrating an alternative method of securement using the securement device.

Turning to FIGS. 1 and 5, the securement device 10 may be used in an alternative way, allowing the securement device to be utilized to secure rigid catheter hubs with short wings, rigid wingless catheter hubs, adequately rigid bifurcation hubs, rigid tubes, or big lumen, thick walled, non-vascular access tubes. In this method, the nurse first positions the securement device 10 between the device to be secured and the patient's skin. Illustratively, in FIG. 5 the device to be secured is shown as a rigid non-winged catheter hub 60. The nurse then removes the release liner 36 to expose the adhesive side 14 of the base 12. While holding the catheter hub 60 and the securement device 10, the nurse affixes the securement device 10 to the patient's skin by contacting the base adhesive side 14 with the patient's skin. Next, with the catheter hub 60 positioned about the slit 20, the nurse pulls one of the gripping tabs 22 over the catheter hub 60. This opens the slit 20 to one side of the catheter hub 60. The nurse then pulls the other gripping tab 22 from generally underneath the first gripping tab 22 through the open slit 20 until the second gripping tab 22 is fixed in place. The second gripping tab 22 is generally fixed in place by the terminal ends of the gripping tab 22 engaging the terminal ends of the slit 20. After completion of this method, the gripping tabs 22 are positioned in a bow tie, half granny knot like arrangement as shown in FIG. 5. The catheter hub 60 and the overlapped gripping tabs 22 should be positioned relative to each other such that the gripping tabs do not extend beyond the rigid catheter hub.

Figure 6:
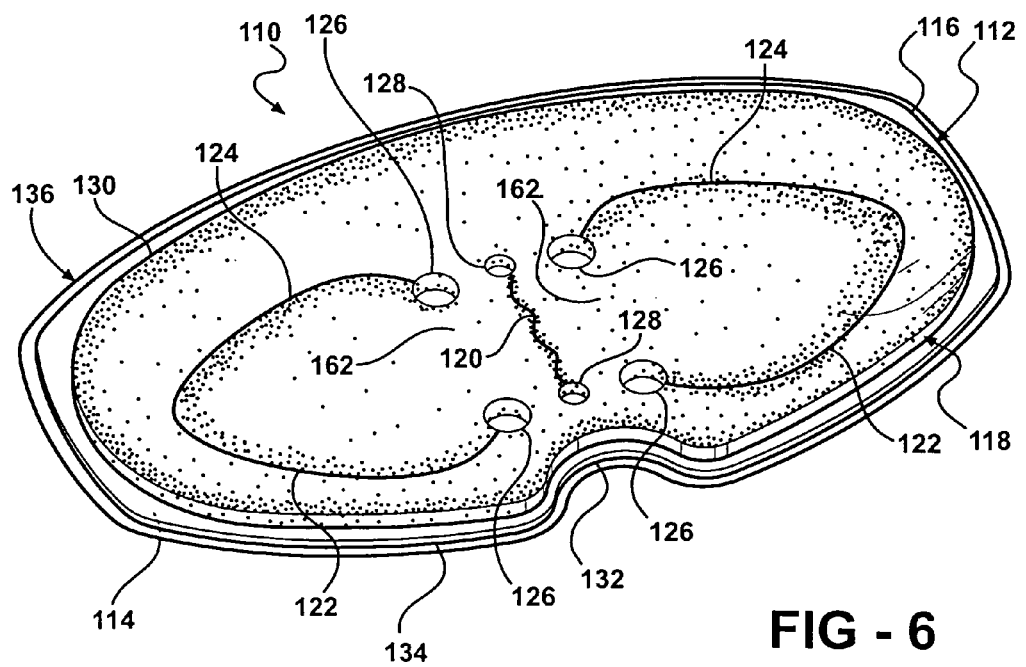
FIG. 6 is a perspective view of an alternative embodiment of a winged securement device in accordance with the present invention.

With reference now to FIG. 6, in an alternative embodiment of the present invention, the gripping tabs 122 of the securement device 110 are of a spade-like shape. This facilitates tab pull-through, which is especially important when securing a device according to the second method above. Further, in the second embodiment of the securement device 110, the apertures 126 at terminal ends of the cut lines 124 defining the tabs 122 are larger than in the first embodiment 10. This makes a foot portion 162 of the gripping tabs 122 narrower than in the first embodiment 10. By decreasing the width of the foot portion 162, an equal amount of pulling force on the gripping tabs 122 opens the slit 120 a larger amount. Therefore, altering the size of the apertures 126 can vary the ease at which, and likewise the amount, a user can open the slit 120. Otherwise, the second embodiment of the securement device 110 has similar features to the first embodiment 10, and similar features are similarly numbered.

Although the invention has been described by reference to a specific embodiment, it should be understood that numerous changes may be made within the spirit and scope of the inventive concepts described. Accordingly, it is intended that the invention not be limited to the described embodiment, but that it have the full scope defined by the language of the following claims.

What is claimed is:

1. A winged securement device comprising:
a flexible base having an adhesive side and an opposite non-adhesive side; and
a generally planar, integral elastomeric anchoring member mounted on said base non-adhesive side;
said anchoring member including a peripheral edge portion, a slit adjacent said base and a pair of opposing gripping tabs formed therein on either side of said slit, said peripheral edge portion circumscribing said gripping tabs;
said anchoring member being adhered to said base along said peripheral edge portion of said anchoring member and not being adhered to said base at an inner portion within said peripheral edge portion;
whereby said gripping tabs may be pulled to open said slit for receiving wings of a catheter hub therein and for securing said wings between said anchoring member and said base.

2. The winged securement device of claim 1, wherein said anchoring member includes cut lines defining said gripping tabs.

3. The winged securement device of claim 2, wherein said cut lines are one of a generally C-shape, U-shape, and spade shape.

4. The winged securement device of claim 2, wherein said anchoring member includes apertures at terminal ends of said cut lines.

5. The winged securement device of claim 1, wherein said anchoring member includes apertures at terminal ends of said slit.

6. The winged securement device of claim 1, wherein said anchoring member is made of one of silicone, polyurethane, and high friction rubber.

7. The winged securement device of claim 1, wherein said base is a foam pad.

8. The winged securement device of claim 1, including a recess in an edge thereof along a line extending through said slit.

9. The winged securement device of claim 1, wherein said securement device is generally oval in shape with said slit generally extending along the minor axis thereof.

10. The winged securement device of claim 1, including a release liner having a tackless side contacting said adhesive side of said base, said release liner generally extending to an edge of said base.

11. The winged securement device of claim 10, wherein said release liner includes a first piece and a second piece, said first and second pieces being folded such that each of said first and second pieces has a tab formed by the fold; whereby one of said pieces can be released from said base without tampering with the other of said pieces.

12. A winged securement device comprising:
a flexible sheet-like base having an adhesive side and an opposite non-adhesive side; and
a generally planar, integral elastomeric anchoring layer member mounted on said base non-adhesive side;
said anchoring member including a peripheral edge portion, at least one slit adjacent said base and a pair of opposing gripping tabs formed therein said member on either side of said slit, said peripheral edge portion circumscribing said gripping tabs, and each gripping tab being adjacent one of said at least one slit;
said anchoring member being adhered to said base along said peripheral edge portion of said anchoring member and not being adhered to said base at an inner portion within said peripheral edge portion;
whereby said gripping tabs may be pulled to open said at least one slit.

13. The winged securement device of claim 12, wherein said anchoring member includes separation lines defining said tabs.

14. The winged securement device of claim 13, wherein said anchoring member includes apertures at terminal ends of said separation lines.

15. The winged securement device of claim 12, wherein said anchoring member includes apertures at terminal ends of each of said at least one slit.

16. The winged catheter securement device of claim 12, wherein said device is formed by one of die-cutting, injection molding, or casting.

* * * * *